United States Patent [19]
Greive

[11] Patent Number: 6,039,722
[45] Date of Patent: Mar. 21, 2000

[54] DEVICE FOR SECURING THE ENDS OF CATHETER GUIDE WIRES

[76] Inventor: Michael Greive, Kirchstrasse 4, D-48308 Ottmarsbocholt, Germany

[21] Appl. No.: 09/137,897

[22] Filed: Aug. 20, 1998

Related U.S. Application Data

[63] Continuation of application No. 08/525,754, filed as application No. PCT/EP94/04054, Dec. 6, 1994, abandoned.

[30] Foreign Application Priority Data

Dec. 23, 1993 [DE] Germany .................. 93 19 838 U

[51] Int. Cl.⁷ .................................................. A61M 25/00
[52] U.S. Cl. ........................ 604/528; 604/165; 604/535; 600/585
[58] Field of Search .................... 604/264, 164, 604/165, 93, 158–160, 170, 174, 177, 178, 523, 528, 533–535; 600/433–435, 585; 128/912; 138/118, 118.1

[56] References Cited

U.S. PATENT DOCUMENTS

| | | |
|---|---|---|
| 4,417,886 | 11/1983 | Frankhouser et al. .................. 604/528 |
| 4,552,554 | 11/1985 | Gould et al. . |
| 4,631,059 | 12/1986 | Wolvek et al. .......................... 604/528 |
| 4,652,256 | 3/1987 | Vaillancourt ............................ 604/528 |
| 4,798,598 | 1/1989 | Bonello et al. .......................... 604/528 |
| 4,844,092 | 7/1989 | Rydell et al. . |
| 4,860,757 | 8/1989 | Lynch et al. . |
| 4,973,329 | 11/1990 | Park et al. .................................. 606/1 |
| 5,147,334 | 9/1992 | Moss ....................................... 604/264 |
| 5,163,921 | 11/1992 | Feiring ................................... 604/247 |
| 5,273,042 | 12/1993 | Lynch et al. . |
| 5,279,573 | 1/1994 | Klosterman ............................. 604/171 |
| 5,279,588 | 1/1994 | Nicoletti et al. ........................ 604/250 |
| 5,282,479 | 2/1994 | Havran . |
| 5,366,444 | 11/1994 | Martin .................................... 604/159 |
| 5,389,087 | 2/1995 | Miraki .................................... 604/247 |
| 5,392,778 | 2/1995 | Horzewski . |
| 5,438,993 | 8/1995 | Lynch et al. . |
| 5,448,993 | 9/1995 | Lynch et al. . |

FOREIGN PATENT DOCUMENTS

| | | |
|---|---|---|
| 0 371 486 | 6/1990 | European Pat. Off. . |
| 0 554 754 A1 | 8/1993 | European Pat. Off. . |
| 93 19 838 | 3/1994 | Germany ..................... A61M 25/01 |
| 2 215 703 | 9/1989 | United Kingdom . |

*Primary Examiner*—Ronald K. Stright, Jr.
*Attorney, Agent, or Firm*—Baker & Daniels

[57] ABSTRACT

Device for securing and, if appropriate, straightening the ends of catheter guide wires. The device has an elongate hollow element open at both ends, with a cylindrical section and a conical section which tapers towards one end. A U-shaped slit which extends in the longitudinal direction is present in the wall of the hollow element, so that a tongue which can be pressed into the inside of the hollow element is formed between the legs of the U-shaped slit which open towards the one end.

5 Claims, 2 Drawing Sheets

DEVICE FOR SECURING THE ENDS OF CATHETER GUIDE WIRES

This is a continuation of application Ser. No. 08/525,754, filed Sep. 12, 1995, now abandoned which is a 371 of PCT/EP94/04054, filed Dec. 6, 1994, now abandoned.

BACKGROUND OF THE INVENTION

The present invention relates to a device for securing and, if appropriate, stretching catheter guide wires, in particular the ends thereof, when these are arranged in tubular packages or so-called dispensers.

In retrograde vascular catheterization by the so-called Seldinger technique, a wire probe or a so-called catheter guide wire is pushed into a-metal cannula left in the vessel, and, after removing the cannula via the guide wire, the catheter is introduced into the vessel. For transportation and for better handling, the catheter guide wires or wire probes are arranged in so-called dispensers in the form of thin plastic tubes, which for the most part are curved in a circular configuration. Due to the inherent tension of the curved guide wires, vibration can lead to at least the end of the guide wires slipping out of the tubular transportation and storage package, so that there is a risk of damage being done. In order to bend or stretch the end of guide wires and to protect them from damage, the company Leake Region Inc., Chaska, Minn., United States offers a hollow element which is pushed into the end of the tubular package (dispenser) of guide wires and in fixed by means of a clamping fit. The hollow element has a cylindrical section and a conical section. Ends of the guide wires, which ends may if appropriate be bent, are staightened or stretched in the longitudinal direction in the hollow element. In order to secure the guide wire against slipping out, the shaft device pushed into the packaging tube has a bore which is adapted to the external diameter of the guide wire and extends in the longitudinal direction. For this reason, this device can be used only in each case to secure guide wires of a specific diameter. For different wire diameters, different securing devices must be produced and kept in stock.

SUMMARY OF THE INVENTION

The object of the invention is to provide a device which can be connected to packaging tubes for catheter guide wires and which reliably protects the end of the guide wires during transportation and storage until they are used, the intention being that wires of different diameters will be fixed securely against displacement in the longitudinal direction.

This object is achieved by means of a device for securing and, if appropriate, stretching the ends of catheter guide wires, the said device comprising an elongate hollow element open at both ends, with a cylindrical section and a conical section which tapers towards the and, characterized in that a U-shaped slit extending in the longitudinal direction in present in the wall, so that a tongue which can be pressed into the inside of the hollow element is formed between the legs of the U-shaped slit which open towards the conical end.

The U-shaped slit can extend either in the area of the cylindrical section or in the area of the conical section, or else over both sections.

When the inwardly pressed tongue makes contact with the catheter guide wire which has been introduced, it secures the said wire against undesired displacement in the longitudinal direction.

In order to improve the securing effect, the tongue can have a kink, so that the free end of the tongue is bent into the inside of the hollow element.

That end of the tongue which is fixed and merges into the wall is preferably situated at the transition from the cylindrical section to the conical section or else in the conical section.

The tongue can be thicker than, thinner than or identical to the wall thickness of the cylindrical section.

In order to facilitate the handling of the device, wings extending laterally from the wall can be provided on the cylindrical section of the hollow element in a plane through the longitudinal axis of the hollow element. The wings can have a square shape, semicircular shape or oval shape.

The internal diameter of the cylindrical section of the device is adapted to the external diameter of the tubular packages of the guide wires, so that the end of the plastic tube can be pushed into the cylindrical section. A clamping fit on the dispenser tube is achieved by virtue of the fact that the device is pushed onto the tube until the tongue is situated in the inside of the tube and, by means of the spring action, fixes the tube end in the cylindrical section of the device. The tongue, which in this way is pressed further inwards, secures the catheter guide wire against displacement in the longitudinal direction. The kink in the tongue acts as a sort of notch for the clamping fit of the device according to the invention on the end of a tubular package for the catheter guide wire. The device according to the invention is made of plastic, preferably, for reasons of cost, by the injection moulding method. Thermoplastic polymers or thermoplastic elastomers are suitable. Especially suitable are polyolefins, for example polypropylene, both low-density and high-density polyethylene, or, alternatively, use can also be made of acrylic-butadione-styrene terpolymers, impact polystyrene or polyoxymethylene. The polymer material exhibits an elasticity which is such that although the tongue is indeed movable, i.e. .is flexible at its point of connection to the hollow element, it at the same time has a sufficient restoring force in order to return to its starting position or to near its starting position when the device is withdrawn from the tubular dispenser.

BRIEF DESCRIPTION OF THE DRAWINGS

The invention, in particular the mode of securing for transportation, is explained in greater detail hereinbelow with reference to the Figures.

DESCRIPTION OF THE PREFERRED EMBODIMENT

Figure 1:
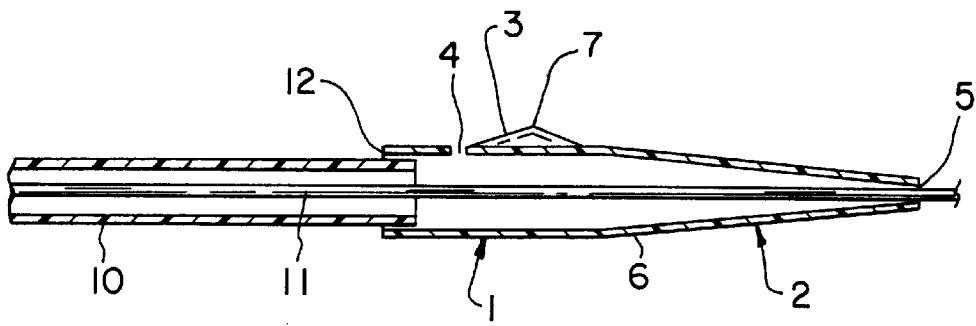
FIG. 1 is a longitudinal section of the device with a catheter guide wire running inside, the device not yet having been pushed completely onto the dispenser tube.

FIG. 1 shows the hollow element according to the invention pushed partially onto the end of the tubular package 10 of the catheter guide wire 11, with a cylindrical section 1 and a conical section 2, the tapered end 5 of which lies opposite the other end 12 of the cylindrical section 1. The conical section 2 is preferably designed longer than the cylindrical section 1. The ratio of the length of the cylindrical section 1 to the length of the conical section 2 can be from 1:1 to 1:3. The device according to the invention is pushed over the end of the catheter guide wire 11, which is protruding from the tube 10, and onto the tube 10. In the sectional view, the open end of the U-shaped slit 4 in the wall 6 of the tubular hollow element in represented on the upper side.

Figure 2:
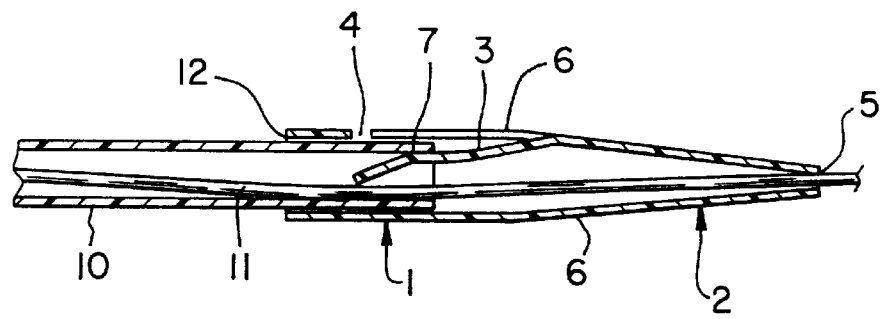
FIG. 2 in a longitudinal section of the device with a guide wire running inside, the device having been pushed onto the dispenser tube to such an extent that the tube presses the tongue inwards and the guide wire is fixed against displacement in the longitudinal direction.
Figure 6:
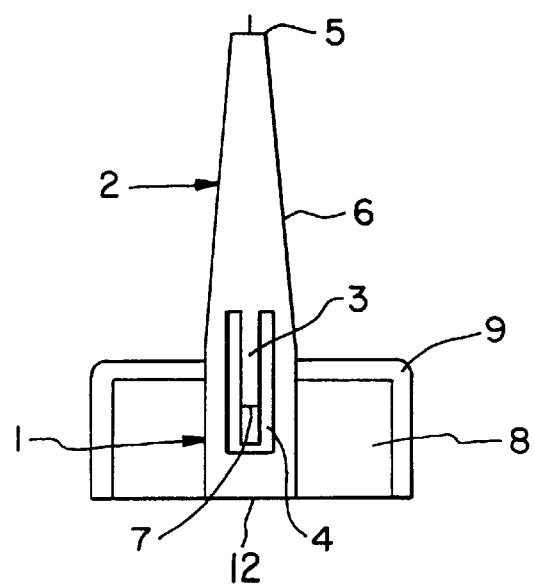
FIG. 6 is a top view of the device showing the U-shaped slit.

FIG. 6 is a top view of the device and clearly shows the U-shaped slit 4 and the movable tongue 3 located between the legs of the U-shaped slit 4. The movable tongue 3 formed from wall material between the legs of the U-shaped slit 4 and with a kink 7 is represented in FIG. 1 in a form in which it is pressed slightly outwards. However, the tongue 3 can be pressed into the inside of the hollow element, with the free end of the tongue preferably being situated slightly within the wall 6 of the hollow element so that, when the device is pushed further onto the tube 10, the tongue 3 pushes into the inside of the storage tube 10, as is represented in FIG. 2. If the tube 10 is pushed over the kink 7 of the tongue 3, the tongue 3 is pressed further inwards by the tube 10 against the catheter guide wire 11 and fixes the latter, inside the device and inside the tube 10, against displacement in the longitudinal direction. The cylindrical part 1 of the hollow element is situated, in the position represented in FIG. 2, in a clamping fit on the tube 10. In FIG. 2, the slit in the wall 6 of the hollow element is again designated by 4. The cylindrical section has the reference number 1, and the conical section the reference number 2. The end of the conical section is designated by 5.

Figure 4:
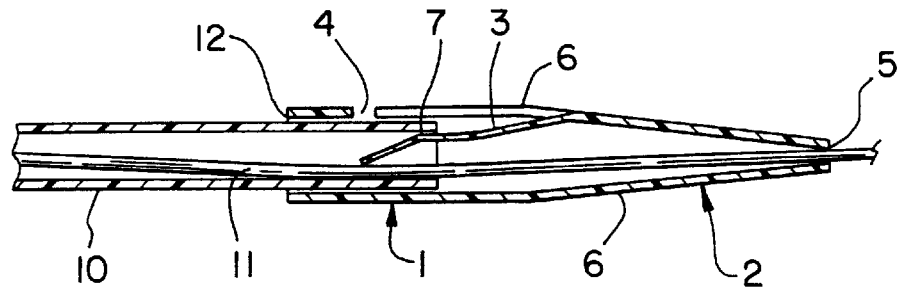
FIG. 4 is a view similar to FIG. 2 except that the tongue is shown as thinner than the wall thickness of the cylindrical section.
Figure 5:
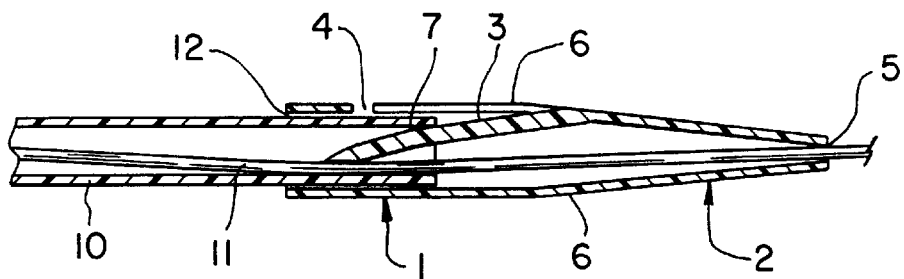
FIG. 5 is similar to FIG. 2 with the exception that the tongue is shown as thicker than the wall thickness of the cylindrical section.

FIG. 4 is similar to FIG. 2 with the exception that tongue 3 is thinner than the thickness of the cylindrical section. FIG. 5 is similar to FIG. 2 with the exception that tongue 3 is thicker than the wall thickness of the cylindrical section.

Figure 3:
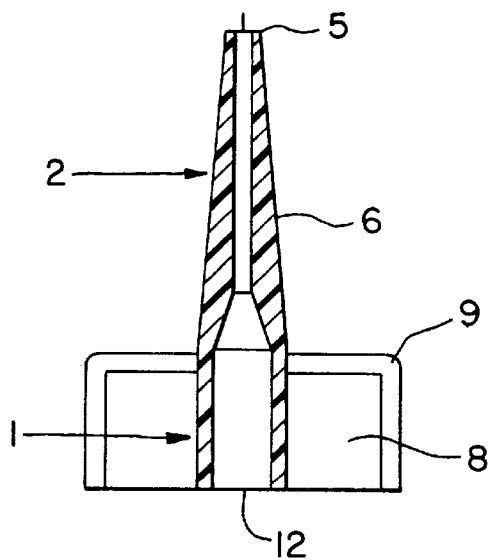
FIG. 3 is a longitudinal section of the device with lateral, rectangular wings.

FIG. 3 shows in particular the inside of the hollow element. The conical section 2 with its end 5 has a continuous inner bore, the diameter of which is greater than the maximum external diameter of catheter guide wires. The cylindrical section 1 has an inner bore which tapers slightly in the direction of the conical section and whose internal diameter at the end 12 is slightly greater than the external diameter of conventional plastic tubes for the packaging of catheter guide wires. At its point of transition to the conical section 2, the inner bore of the cylindrical section tapers to the diameter of the inner bore of the conical section 2. In FIG. 3, moreover, the wings 8 extending laterally from the wall 6 are represented with a reinforcement edge 9.

Conventional plastic tubes for receiving catheter guide wires have an external diameter of 2 to 6 mm, so that the device according to the invention has an internal diameter of 2 to 6 mm at the end 12 in the cylindrical section. The internal diameter of the longitudinal bore in the conical section 2 of the hollow element normally amounts to 1 to 2 mm.

The wall thickness of the device according to the invention depends first and foremost on the required stability and flexibility of the material used, with wall thicknesses of 0.5 to 1.5 mm being preferred.

When using the device according to the invention in the Seldinger technique, the conical section 2 of the device according to the invention is pushed into the rear end of a metal cannula lying in the vessel. After the storage tube 10 has been withdrawn from the device according to the invention, the catheter guide wire 11 is freely movable and can be pushed through the hollow element into the metal cannula and onwards into the vessel.

Furthermore, in the event of the catheter guide wires having curved tips, the hollow cylindrical bore in the conical section 2 of the hollow element has the effect of bending, straightening or stretching these in the longitudinal direction, so that a smooth transfer into the metal cannula lying in the vessel is possible.

The greater internal diameter in the area of the cylindrical section of the hollow element and the tapering of the bore towards the conical section makes it easier to push the device according to the invention onto the ends, which may be curved, of catheter guide wires.

List of References

1 Cylindrical section of the hollow element
2 Conical section of the hollow element
3 Tongue
4 U-shaped slit
5 End of the conical section
6 Wall
7 Kink in the tongues
8 Wings
9 Edging
10 Dispenser tube
11 Guide wire
12 End of the cylindrical section of the hollow element

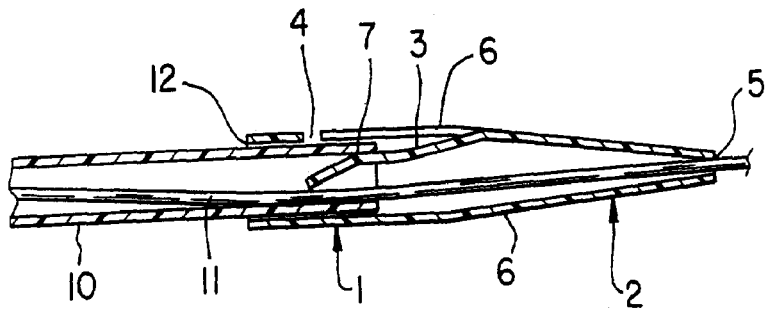

I claim:

1. An apparatus for straightening the end of a catheter guide wire, said apparatus comprising;

an elongate tube for storing a catheter guide wire, said tube having end;

an elongate hollow element open at both ends, said element including a cylindrical section dimensioned to receive said end of said tube, and a conical section which tapers in a direction away from said cylindrical section, a U-shaped slit in the wall of said hollow elongate element and extending in the longitudinal direction of said hollow element and defining a first edge, the legs of said U-shaped slit defining a flexible tongue having two ends, said tongue secured at a first end to said wall, the second end of said tongue is free, at least a portion of said tongue depressable into said hollow element, substantially parallel to the longitudinal direction of said elongate hollow element, said at least a portion of said tongue received in said end of said tube, whereby said tongue engages a catheter guide wire stored in said tube to prevent displacement of said catheter guide wire in said longitudinal direction.

2. The apparatus according to claim 1 including a plurality of wings extending laterally from said cylindrical section, said wings oriented in a plane which intersects the longitudinal axis of said hollow element.

3. The apparatus according to claim 1 wherein said tongue includes a kink.

4. The apparatus according to claim 1 wherein said tongue is thicker than the wall thickness of said tubular section.

5. The apparatus according to claim 1 wherein said hollow element is made of a thermo plastic polymer or thermo plastic elastomer.

* * * * *

UNITED STATES PATENT AND TRADEMARK OFFICE
CERTIFICATE OF CORRECTION

PATENT NO.   : 6,039,722
DATED        : March 21, 2000
INVENTOR(S)  : Michael Greive It is certified that error appears in the above-identified patent and that said Letters Patent is hereby corrected as shown below:

The title page should be deleted to appear as per attached title page.

Signed and Sealed this

Seventeenth Day of December, 2002

JAMES E. ROGAN
*Director of the United States Patent and Trademark Office*

United States Patent [19]

Greive

[11] Patent Number: 6,039,722

[45] Date of Patent: Mar. 21, 2000

[54] DEVICE FOR SECURING THE ENDS OF CATHETER GUIDE WIRES

[76] Inventor: Michael Greive, Kirchstrasse 4, D-48308 Ottmarsbocholt, Germany

[21] Appl. No.: 09/137,897

[22] Filed: Aug. 20, 1998

Related U.S. Application Data

[63] Continuation of application No. 08/525,754, filed as application No. PCT/EP94/04054, Dec. 6, 1994, abandoned.

[30] Foreign Application Priority Data

Dec. 23, 1993 [DE] Germany .......................... 93 19 838 U

[51] Int. Cl.$^7$ ................................................. A61M 25/00
[52] U.S. Cl. ........................... 604/528; 604/165; 604/535; 600/585
[58] Field of Search ................................ 604/264, 164, 604/165, 93, 158–160, 170, 174, 177, 178, 523, 528, 533–535; 600/433–435, 585; 128/912; 138/118, 118.1

[56] References Cited

U.S. PATENT DOCUMENTS

| | | |
|---|---|---|
| 4,417,886 | 11/1983 | Frankhouser et al. ............... 604/528 |
| 4,552,554 | 11/1985 | Gould et al. . |
| 4,631,059 | 12/1986 | Wolvek et al. ........................ 604/528 |
| 4,652,256 | 3/1987 | Vaillancourt ......................... 604/528 |
| 4,798,598 | 1/1989 | Bonello et al. ....................... 604/528 |
| 4,844,092 | 7/1989 | Rydell et al. . |
| 4,860,757 | 8/1989 | Lynch et al. . |
| 4,973,329 | 11/1990 | Park et al. ............................. 606/1 |
| 5,147,334 | 9/1992 | Moss ..................................... 604/264 |
| 5,163,921 | 11/1992 | Feiring ................................. 604/247 |
| 5,273,042 | 12/1993 | Lynch et al. . |
| 5,279,573 | 1/1994 | Klosterman ......................... 604/171 |
| 5,279,588 | 1/1994 | Nicoletti et al. .................... 604/250 |
| 5,282,479 | 2/1994 | Havran . |
| 5,366,444 | 11/1994 | Martin ................................. 604/159 |
| 5,389,087 | 2/1995 | Miraki ................................. 604/247 |
| 5,392,778 | 2/1995 | Horzewski . |
| 5,438,993 | 8/1995 | Lynch et al. . |
| 5,448,993 | 9/1995 | Lynch et al. . |

FOREIGN PATENT DOCUMENTS

| | | |
|---|---|---|
| 0 371 486 | 6/1990 | European Pat. Off. . |
| 0 554 754 A1 | 8/1993 | European Pat. Off. . |
| 93 19 838 | 3/1994 | Germany ...................... A61M 25/01 |
| 2 215 703 | 9/1989 | United Kingdom . |

*Primary Examiner*—Ronald K. Stright, Jr.
*Attorney, Agent, or Firm*—Baker & Daniels

[57] ABSTRACT

Device for securing and, if appropriate, straightening the ends of catheter guide wires. The device has an elongate hollow element open at both ends, with a cylindrical section and a conical section which tapers towards one end. A U-shaped slit which extends in the longitudinal direction is present in the wall of the hollow element, so that a tongue which can be pressed into the inside of the hollow element is formed between the legs of the U-shaped slit which open towards the one end.

5 Claims, 2 Drawing Sheets